(12) United States Patent
Herz et al.

(10) Patent No.: US 8,707,767 B2
(45) Date of Patent: Apr. 29, 2014

(54) COMBINED HYDROGEN AND PRESSURE SENSOR ASSEMBLY

(75) Inventors: Joshua J. Herz, Rochester, NY (US); David Billings, Spencerport, NY (US)

(73) Assignee: Qualitrol Company, LLC, Fairport, NY (US)

( * ) Notice: Subject to any disclaimer, the term of this patent is extended or adjusted under 35 U.S.C. 154(b) by 502 days.

(21) Appl. No.: 13/076,617

(22) Filed: Mar. 31, 2011

(65) Prior Publication Data

US 2012/0247191 A1    Oct. 4, 2012

(51) Int. Cl.
*G01N 37/00* (2006.01)

(52) U.S. Cl.
USPC ........................................................ 73/61.43

(58) Field of Classification Search
USPC ........................................................ 73/61.43
See application file for complete search history.

(56) References Cited

U.S. PATENT DOCUMENTS

| | | |
|---|---|---|
| 3,559,457 A | 2/1971 | Collins |
| 3,927,555 A | 12/1975 | Godwin et al. |
| 4,112,737 A | 9/1978 | Morgan |
| 4,271,474 A | 6/1981 | Belanger et al. |
| 4,293,399 A | 10/1981 | Belanger et al. |
| 4,654,806 A | 3/1987 | Poyser et al. |
| 5,070,738 A | 12/1991 | Morgan |
| 5,271,263 A | 12/1993 | Gibeault |
| 5,339,672 A | 8/1994 | Spicar |
| 5,659,126 A | 8/1997 | Farber |
| 5,749,942 A | 5/1998 | Mattis et al. |
| 5,773,709 A | 6/1998 | Gibeault et al. |

(Continued)

FOREIGN PATENT DOCUMENTS

| | | | |
|---|---|---|---|
| JP | 62-249045 A | | 10/1987 |
| JP | 2004279063 A | | 10/2004 |
| KR | 10-2002-0029819 A | | 5/2002 |
| KR | 10-0811684 B1 | | 3/2008 |

OTHER PUBLICATIONS

PCT-Notification of Transmittal of the International Search Report and the Written Opinion of the International Searching Authority, or the Declaration; dated Nov. 1, 2012 (2 pages) (in International Patent Application No. PCT/US2012/030321).

(Continued)

*Primary Examiner* — Hezron E Williams
*Assistant Examiner* — Rodney T Frank
(74) *Attorney, Agent, or Firm* — Brian B. Shaw, Esq.; Paul A. Leipold, Esq.; Harter Secrest & Emery LLP

(57) ABSTRACT

A housing sensor having a semiconductor element for measuring hydrogen concentration in an insulating fluid in equipment having a mounting flange on the equipment providing access to the interior of the equipment provided with a plurality of bolt receiving openings arranged on the mounting flange in a first pattern which includes a first flange having at least one or more openings and an outer periphery. The sensor also includes a tubular housing support member having one end received in one of the openings, a plurality of bolt receiving apertures arranged in a pattern corresponding to the first pattern within the outer periphery of the first flange. The sensor further includes at least one wire receiving opening extending through the housing body, a cover closing an end of the housing body distal from the one end, a first seal disposed between the first flange and the tubular housing support member, a second seal disposed on the first flange for engaging the mounting flange.

5 Claims, 3 Drawing Sheets

(56) References Cited

U.S. PATENT DOCUMENTS

| | | | |
|---|---|---|---|
| 6,037,592 | A | 3/2000 | Sunshine et al. |
| 6,446,027 | B1 | 9/2002 | O'Keeffe et al. |
| 6,906,630 | B2 | 6/2005 | Georges et al. |
| 7,228,725 | B2 | 6/2007 | Salter et al. |
| 7,249,490 | B2 | 7/2007 | Pendergrass |
| 7,268,662 | B2 | 9/2007 | Hines et al. |
| 7,565,827 | B2 | 7/2009 | Salter et al. |
| 7,747,417 | B2 | 6/2010 | Lamontagne |
| 2003/0029228 | A1 | 2/2003 | Bloder et al. |
| 2004/0261500 | A1 | 12/2004 | Ng et al. |
| 2005/0086998 | A1 | 4/2005 | Qin |
| 2005/0241382 | A1 | 11/2005 | Coenen |
| 2007/0068493 | A1 | 3/2007 | Pavlovsky |
| 2007/0125153 | A1 | 6/2007 | Visel et al. |
| 2007/0240491 | A1 | 10/2007 | Pavlovsky et al. |
| 2009/0301879 | A1 | 12/2009 | Soundarrajan et al. |
| 2010/0077828 | A1 | 4/2010 | Herz et al. |

OTHER PUBLICATIONS

PCT-International Search Report; dated Nov. 1, 2012 (3 pages) (in International Patent Application No. PCT/US2012/030321).

PCT-Written Opinion of the International Searching Authority; dated Nov. 1, 2012 (4 pages) (in International Patent Application No. PCT/US2012/030321).

PCT-Notification of Transmittal of the International Search Report and the Written Opinion of the International Searching Authority, or the Declaration; dated Mar. 11, 2010 (4 pages) (in International Patent Application No. PCT/US2009/054151).

PCT-International Search Report; dated Mar. 11, 2010 (3 pages) (in International Patent Application No. PCT/US2009/054151).

PCT-Written Opinion of the International Searching Authority; dated Mar. 11, 2010 (4 pages) (in International Patent Application No. PCT/US2009/054151).

Cargol, Tim, "An Overview of Online Oil Monitoring Technologies", Weidmann-ACTI, Inc., Fourth Annual Weidmann-ACTI Technical Conference, San Antonio, 2005, pp. 1-6.

Pavlovsky et al., "Palladium Nanoparticle Hydrogen Sensor", Gases & Technology Feature Jul./Aug. 2006, pp. 18-21.

Gas and Moisture Monitor GMM, Tree Tech Sistemas Digitais, CA-029, Jul. 20, 2006 Rev. 2, pp. 1-6.

Serveron, "Reliable energy through cost effective, on-line DGA", products and information (6 pages).

GE HydranMs Sensor, Technical Specifications, Appendix A, Part 16374, Rev. 2, Jul. 2005, A-1. pp. A1-A10.

Calisto, Dissolved Hydrogen and Water Monitor, Morgan Schaffer Systems, Transformers-The inside View (7 pages).

COMBINED HYDROGEN AND PRESSURE SENSOR ASSEMBLY

CROSS-REFERENCE TO RELATED APPLICATIONS

None.

FIELD OF THE INVENTION

This invention relates to the sensing of hydrogen in oils. It particularly relates to apparatus for sensing of hydrogen in electric power generation transmission and distribution equipment oil.

BACKGROUND OF THE INVENTION

Electrical equipment, particularly medium-voltage or high-voltage electrical equipment, requires a high degree of electrical and thermal insulation between components thereof. Accordingly, it is well known to encapsulate components of electrical equipment, such as coils of a transformer, in a containment vessel and to fill the containment vessel with a fluid. The fluid facilitates dissipation of heat generated by the components and can be circulated through a heat exchanger to efficiently lower the operating temperature of the components. The fluid also serves as electrical insulation between components or to supplement other forms of insulation disposed around the components, such as cellulose paper or other insulating materials. Any fluid having the desired electrical and thermal properties can be used. Typically, electrical equipment is filled with an oil, such as castor oil, mineral oil, or vegetable oil, or a synthetic "oil", such as chlorinated diphenyl, silicone, or sulfur hexafluoride.

Often, electrical equipment is used in a mission-critical environment in which failure can be very expensive, or even catastrophic, because of a loss of electric power to critical systems. In addition, failure of electrical equipment ordinarily results in a great deal of damage to the equipment itself and surrounding equipment thus requiring replacement of expensive equipment. Further, such failure can cause injury to personnel due to electric shock, fire, or explosion. Therefore, it is desirable to monitor the status of electrical equipment to predict potential failure of the equipment through detection of incipient faults and to take remedial action through repair, replacement, or adjustment of operating conditions of the equipment. However, the performance and behavior of fluid-filled electrical equipment inherently degrades over time. Faults and incipient faults should be distinguished from normal and acceptable degradation.

A known method of monitoring the status of fluid-filled electrical equipment is to monitor various parameters of the fluid. For example, the temperature of the fluid and the total combustible gas (TCG) in the fluid is known to be indicative of the operating state of fluid-filled electrical equipment. Therefore, monitoring these parameters of the fluid can provide an indication of any incipient faults in the equipment. For example, it has been found that carbon monoxide and carbon dioxide increase in concentration with thermal aging and degradation of cellulosic insulation in electrical equipment. Hydrogen and various hydrocarbons (and derivatives thereof such as acetylene and ethylene) increase in concentration due to hot spots caused by circulating currents and dielectric breakdown such as corona and arcing. Concentrations of oxygen and nitrogen indicate the quality of the gas pressurizing system employed in large equipment, such as transformers. Accordingly, "dissolved gas analysis" (DGA) has become a well-accepted method of discerning incipient faults in fluid-filled electric equipment.

In conventional DGA methods, an amount of fluid is removed from the containment vessel of the equipment through a drain valve. The removed fluid is then subjected to testing for dissolved gas in a lab or by equipment in the field. This method of testing is referred to herein as "offline" DGA. Since the gases are generated by various known faults, such as degradation of insulation material or other portions of electric components in the equipment, turn-to-turn shorts in coils, overloading, loose connections, or the like, various diagnostic theories have been developed for correlating the quantities of various gases in fluid with particular faults in electrical equipment in which the fluid is contained. However, since conventional methods of off-line DGA require removal of fluid from the electric equipment, these methods do not, 1) yield localized position information relating to any fault in the equipment, 2) account for spatial variations of gases in the equipment, and 3) provide real time data relating to faults. If analysis is conducted off site, results may not be obtained for several hours. Incipient faults may develop into failure of the equipment over such a period of time.

The measurement of hydrogen gas in the oil of an electrical transformer is of interest as it is an indication of the breakdown of the oil caused by overheating and/or arcing inside the transformer. Transformer oil cools the transformer and acts as a dielectric. As transformer oil ages it becomes a less effective dielectric. The increase in hydrogen dissolved in the transformer oil is an indicator of the coming failure of the transformer.

For large transformers there are hydrogen sensors that use gas chromatography or photo-acoustic spectroscopy to determine the amount of hydrogen gas within a transformer's oil. Such devices are very expensive and the expense is not justified for smaller transformers. There are many older, small transformers that could be monitored if a low-cost method of doing so was available.

A lower-cost gas monitor, the Hydran™ M2 manufactured by General Electric Company has been in use. However, this gas monitor only senses combustible gases and then uses a formula to estimate how much of the gas typically is hydrogen and how much is other gases.

An article "Overview of Online Oil Monitoring Technologies" by Tim Cargol at the Fourth Annual Weidmann-ACTI Technical Conference, San Antonio 2005 provides a discussion of oil gas measuring techniques, including hydrogen measurement.

Palladium hydrogen sensors are disclosed in Gases and Technology, July/August 2006, in the article, "Palladium Nanoparticle Hydrogen Sensor" pages 18-21. Palladium sensors are also disclosed in U.S. Patent Publications 2007/0125153-Visel et al., 2007/0068493-Pavlovsky, and 2004/0261500-Ng et al. U.S. Patent Application No. 2010/007828 discloses a hydrogen sensor for an electrical transformer.

There is a need for low-cost method of determining hydrogen gas content in oils, such as in electric power generation and transmission and distribution equipment especially transformers. There is a particular need for a method and apparatus for mounting a hydrogen sensor to electric power generation transmission and distribution equipment that does not require taking the equipment out of service and preferably uses existing fittings or ports in the equipment without the necessity of making new openings in the housings for the equipment. It would particularly advantageous to provide a method and apparatus for attaching a hydrogen sensor to a transformer or the like using the port used for a pressure sensor especially a rapid pressure rise sensor.

BRIEF SUMMARY OF THE INVENTION

The invention provides a sensor housing having a semiconductor element for measuring hydrogen concentration in an insulating fluid in electric power generation, transmission, and distribution equipment having a mounting flange on the equipment providing access to the interior of the equipment provided with a plurality of bolt receiving openings arranged on the mounting flange in a first pattern which includes a first flange having at least one or more openings and an outer periphery. The invention includes a tubular housing support member having one end received in one of the openings, a plurality of bolt receiving apertures arranged in a pattern corresponding to the first pattern within the outer periphery of the first flange. The invention further includes a housing body having one end thereof connected to the tubular housing support member and disposed among the bolt receiving apertures, and spaced therefrom a sufficient distance to allow access to bolts disposed in the openings for inserting and removing bolts from the openings and having an outer periphery contained within the outer periphery of the first flange and further having a substantially uniform cross-section extending from the tubular housing support member, at least one wire receiving opening extending through the housing body, a cover closing an end of the housing body distal from the one end, a first seal disposed between the first flange and the tubular housing support member, a second seal disposed on the first flange for engaging the mounting flange, and a sampling and bleeding valve extending through the first flange in communication with the interior of the equipment and oriented so that when opened trapped gas will exit the valve.

BRIEF DESCRIPTION OF THE SEVERAL VIEWS OF THE DRAWING(S)

DETAILED DESCRIPTION OF THE INVENTION

The invention provides numerous advantages over prior apparatus. The invention is smaller, easily installed, and lower in cost than other hydrogen sensing devices. The device is accurate and can be easily retrofitted onto existing transformers or engines. The device provides a very accurate hydrogen sensor with real time results as removal of fluid is not required. The device allows replacement of the sensor without providing a significant opening for oil to leave the container. The invention sensor utilizes instrument controls that are well known and available. These and other advantages will be apparent from the description below.

The invention provides easy retrofit of the hydrogen sensor to the transformer as an opening in the transformer housing is already present. This also is lower in cost than if a new inlet to the transformer needed to be installed. Further, the installation of the invention is low maintenance and will work at higher temperatures such as 120° C.

Figure 1:
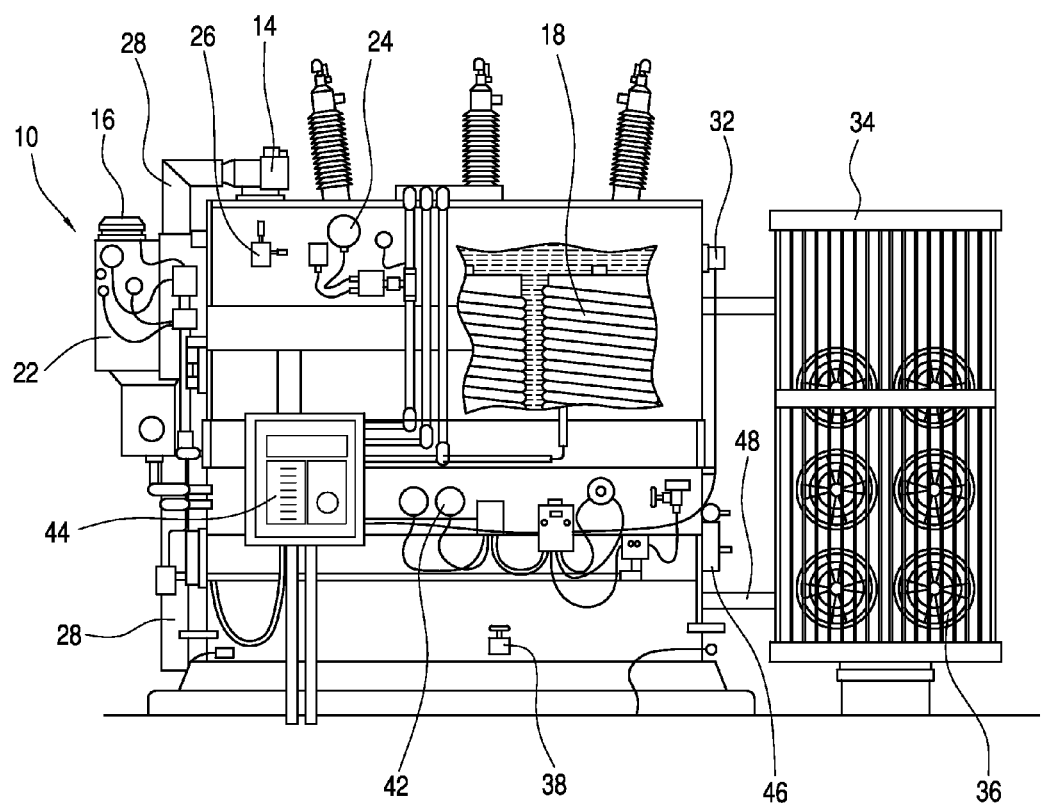
FIG. 1 is a view of a transformer indicating possible locations for the attachments for sensors.

Illustrated in FIG. 1 is a transformer 10. The transformer 10 is provided with pressure relief devices 14 and 16. The transformer 10 is partially cutaway to show the coils 18. The transformer 10 has a temperature gauge 24. The temperature gauge 26 measures the temperature of the oil of the transformer. The pipe terminal 28 connects to the overflow pipe leading from pressure relief device 14. The optical fiber entry 32 provides direct reading of the winding temperature. A cooling tower 34 is utilized to regulate the temperature of the oil in the transformer by cooling when necessary using fans 36. The drain valve 38 is utilized to drain the oil for changing or to secure test samples. Electromechanical thermometers 42 sense the temperature of the oil in the transformer. The IED intelligent electronic device 44 controls the sensing devices and provides readouts of the information sensed. It further may control the cooling of the reactor as necessary. A rapid pressure rise relay 46 is also provided on the transformer. A flow gauge, not shown may be provided at location 48. The various temperature and pressure sensors, pressure release devices, drains, and flow gauges may provide mounting areas for hydrogen sensors.

Figure 2:
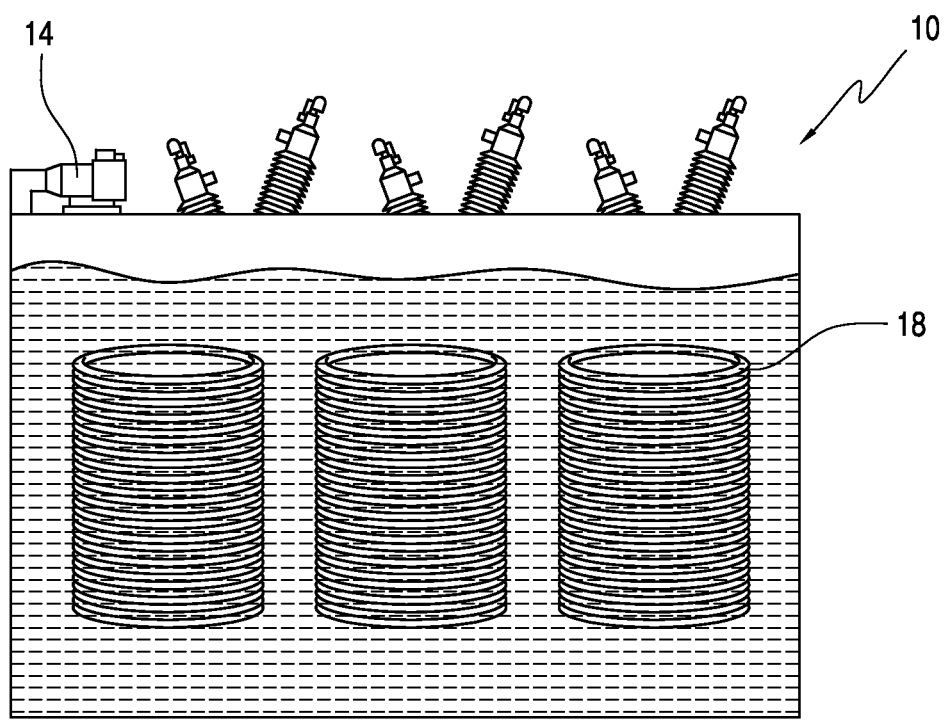
FIG. 2 is a view of a transformer indicating a location for a sensor.

FIG. 2 shows a transformer 10 having a pressure release device 14 on the top of the transformer.

Figure 3:
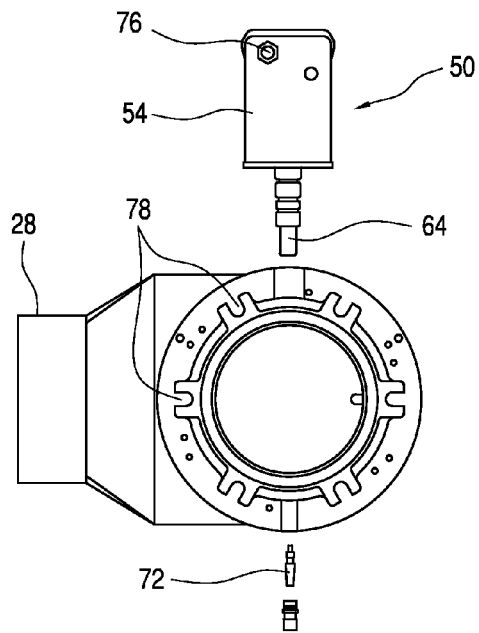
FIGS. 3 and 4 are top and side views of the mounting of the sensor located FIG. 2.
Figure 4:
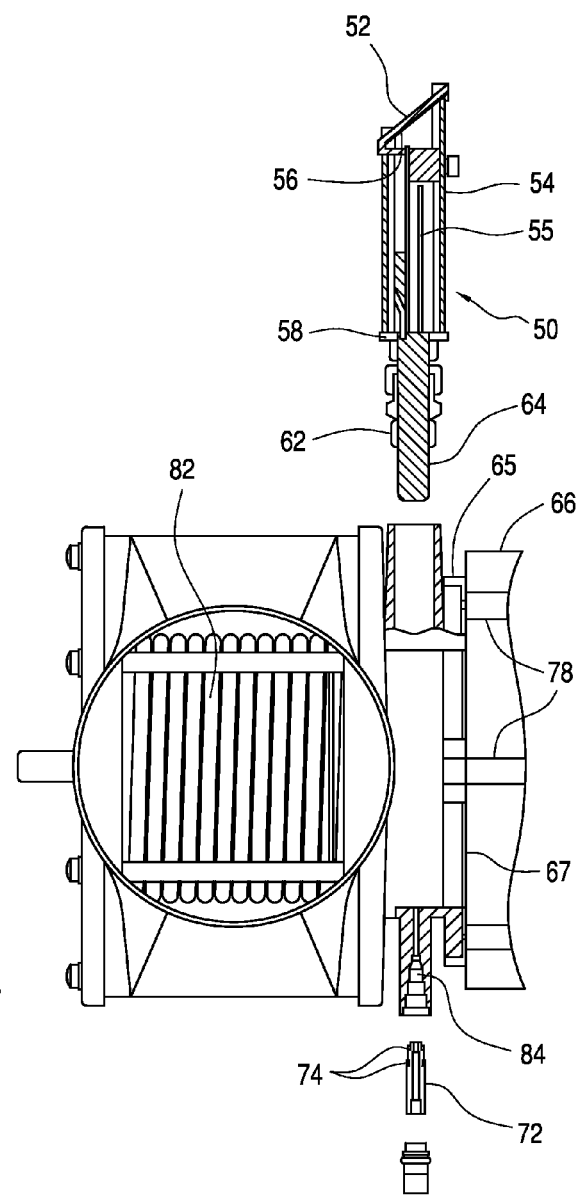

FIGS. 3 and 4 are cross-sectional views illustrating the mounting of a sensor below the pressure relief device 14. Illustrated in FIG. 3 is the housing 54 for the hydrogen sensor. The housing has wires 76 to provide power and read information from the sensor. The pressure release device 14 has a pipe 28 connected thereto where overflow oil would exit the pressure relief valve. There are receiving apertures 78 provided that allow the pressure release device 14 and flanges 65 bearing the hydrogen sensor 50 and sampling and bleeding valve 72 to be installed on the transformer 10.

In FIG. 4, the hydrogen sensor 50 is shown in more detail. Housing 54 is a housing for semiconductor element 55. The sensor has a tubular support 64 for containing the hydrogen sensor. The lid 52 of housing 54 has a seal 56. Housing 54 has a lower seal 58. Sensor seal 62 provides a first seal between the first flange 65 and the tubular support member 64. The seal 62 comprises a tapered thread seal. Mounting flange 66 provides access to the interior of the transformer. The first flange 65 has openings in its periphery for mounting the hydrogen sensor 50 and the sampling and bleeding valve 72. The first flange 65 also has holes for the bolts holding the flange to pass through. There is a sealant on gasket 67 between the first flange 65 and the mounting flange 66. The bolt receiving apertures 78 are arranged in a pattern corresponding to the pattern within the outer periphery of the first flange and serve to hold the pressure relief device in place as well as the flange carrying the hydrogen sensor.

As is apparent from the drawings the placement of the first flange 65, between the mounting flange 66 and the pressure relief device 13 allows placement of the oxygen sensor without the formation of an additional hole in the transformer. The location of the pressure release device 13 at the top of the transformer in some cases may allow sampling of gaseous hydrogen in the open space above the liquid coolant. Other locations would place the hydrogen sensor in the liquid coolant. Sensors are known for sensing hydrogen in liquid as well as in gas and selection of the proper sensor would be within the skill of the art depending upon what type of transformer is utilized and the level of the transformer oil. It is noted that for accurate sensing of the hydrogen content in gas, the pressure of the gas also needs to be sensed. This may be done with the pressure relief device 13 or another pressure gauge (not shown) in the gas above the oil in the transformer.

The sampling valve 72 extends through an edge of the first flange 65 and communicates with a surface of the flange opposite the housing body and communicates with an opening exposed to the interior of the transformer equipment through the mounting flange 66.

Palladium containing hydrogen sensors and controllers for the sensors are known in the art. Such sensors are disclosed in United States Patent Publication Nos. 2007/0125153-Visel et al. and 2007/0240491-Pavlovsky, hereby incorporated by reference. An article in Gases and Technology, July/August 2006 "Palladium Nanoparticle Hydrogen Sensor" by I. Pavlovsky, also contains a description of hydrogen sensors and the methods and apparatus for their use. The palladium nanoparticles utilized in these preferred sensors for the invention are intrinsically sensitive to hydrogen and sensors based on palladium nanoparticle networks do not produce false alarms in the presence of other gases. This makes them particularly desirable for use in the devices of the invention as other gases may be present when the hydrogen is sensed. Other hydrogen sensors and their controllers are disclosed in U.S. Patent Publication Nos. 2007/0068493-Pavlovsky and 2007/0240491-Pavlosky et al., also incorporated herein by reference. The preferred hydrogen sensor for the instant invention is a semi-conductor palladium based hydrogen-type sensor as it is accurate.

While the drawings illustrate the attachment of the hydrogen, sensing device to a flange space between the transformer and the pressure release device this mounting method could be utilized at other locations on the transformer where there is a flange opening and space for the hydrogen sensor. Other locations to consider would be on the load tap changer 22, the drain valve 38 and the rapid pressure rise relay 46. The rapid rise pressure relay 46 provides a good alternative place to mount the hydrogen sensor as it is under the oil and has an isolation valve.

The hydrogen sensor extends through the edge of the flange 65 and may extend beyond the surface of the flange 65. The seal 62 extends around the tubular support member 64 and fits sincerely within the flange 65.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

The invention claimed is:

1. A sensor having a semiconductor element for measuring hydrogen concentration in an insulating fluid in electric power generation, transmission, and distribution equipment having a mounting flange on the equipment providing access to the interior of the equipment provided with a plurality of bolt receiving openings arranged on the mounting flange in a first pattern comprising:
    (a) a first flange having at least one or more openings and an outer periphery;
    (b) a tubular housing support member having one end received in one of the openings;
    (c) a plurality of bolt receiving apertures arranged in a pattern corresponding to the first pattern within the outer periphery of the first flange;
    (d) a housing body having one end thereof connected to the tubular housing support member and disposed among the bolt receiving apertures, and spaced therefrom a sufficient distance to allow access to bolts disposed in the openings for inserting and removing bolts from the openings and having an outer periphery contained within the outer periphery of the first flange and further having a substantially uniform cross-section extending from the tubular housing support member;
    (e) at least one wire receiving opening extending through the housing body;
    (f) a cover closing an end of the housing body distal from the one end;
    (g) a first seal disposed between the first flange and the tubular housing support member;
    (h) a second seal disposed on the first flange for engaging the mounting flange; and
    (i) a sampling and bleeding valve extending through the first flange in communication with the interior of the equipment and oriented so that when opened trapped gas will exit the valve.

2. The sensor of claim 1, wherein the first seal comprises a tapered thread seal.

3. The sensor of claim 1, wherein the sampling valve extends through an edge of the flange and communicates with a surface of the flange opposite the housing body.

4. The sensor assembly of claim 1, wherein the sampling valve communicates with an opening exposed to the interior of the equipment.

5. A sensor having a semiconductor element for measuring hydrogen concentration in an insulating fluid in equipment having a mounting flange on the equipment providing access to the interior of the equipment provided with a plurality of bolt receiving openings arranged on the mounting flange in a first pattern comprising:
    (a) a first flange having at least one or more openings and an outer periphery;
    (b) a tubular housing support member having one end received in one of the openings;
    (c) a plurality of bolt receiving apertures arranged in a pattern corresponding to the first pattern within the outer periphery of the first flange;
    (d) a housing body having one end thereof connected to the tubular housing support member and disposed among the bolt receiving apertures, and spaced therefrom a sufficient distance to allow access to bolts disposed in the openings for inserting and removing bolts from the openings and having an outer periphery contained within the outer periphery of the first flange and further having a substantially uniform cross-section extending from the tubular housing support member;
    (e) at least one wire receiving opening extending through the housing body;
    (f) a cover closing an end of the housing body distal from the one end;
    (g) a first seal disposed between the first flange and the tubular housing support member;
    (h) a second seal disposed on the first flange for engaging the mounting flange; and
    (i) a sampling and bleeding valve extending through the first flange in communication with the interior of the equipment and oriented so that when opened trapped gas will exit the valve.

* * * * *